United States Patent [19]

Heller et al.

[11] Patent Number: 4,710,497

[45] Date of Patent: Dec. 1, 1987

[54] METHOD FOR PERCUTANEOUSLY ADMINISTERING PHYSIOLOGICALLY ACTIVE AGENTS

[75] Inventors: Jorge Heller, Woodside; Wilfred A. Skinner, Portola Valey; Kenichiro Saito, Menlo Park, all of Calif.; Susumu Satoh, Osaka, Japan

[73] Assignee: Nitto Electric Industrial Co., Ltd., Osaka, Japan

[21] Appl. No.: 739,790

[22] Filed: May 31, 1985

Related U.S. Application Data

[63] Continuation-in-part of Ser. No. 729,023, Apr. 30, 1985, abandoned, which is a continuation of Ser. No. 496,732, May 20, 1983, abandoned.

[51] Int. Cl.⁴ ............................................. A61K 31/55
[52] U.S. Cl. ..................................... 514/221; 514/947
[58] Field of Search ............................... 514/947, 221

[56] References Cited

U.S. PATENT DOCUMENTS 4,038,417  7/1977  Nelson ................................. 424/300
4,039,664  8/1977  Stoughton et al. ................. 424/180
4,232,006  11/1980 Taplin et al. ......................... 424/177

OTHER PUBLICATIONS

Lachman et al—"The Theory & Practice of Industrial Pharmacy", 2nd ed., pp. 217–220, 1976.
Merck Index, 9th ed., 1976, p. 684 (#5075).

*Primary Examiner*—Leonard Schenkman
*Attorney, Agent, or Firm*—Sughrue, Mion, Zinn, Macpeak and Seas

[57] ABSTRACT

A method of percutaneously administering a physiologically active agent which comprises applying to the skin of a mammal a physiologically active agent in a carrier system which comprises at least one adjuvant and at least one solvent. The adjuvant can be selected from aliphatic hydrocarbons, halogen substituted aliphatic hydrocarbons, alcohol esters of aliphatic carboxylic acids, mono- or di-ethers, ketones, or mixtures thereof. The solvent can be selected from thioglycerols, lactic acid and esters thereof, cyclic ureas, compounds represented by the general formula $R_1R_2NCONR_3R_4$, pyrrolidone-type compounds, amides, lactones or mixtures thereof.

8 Claims, 1 Drawing Figure

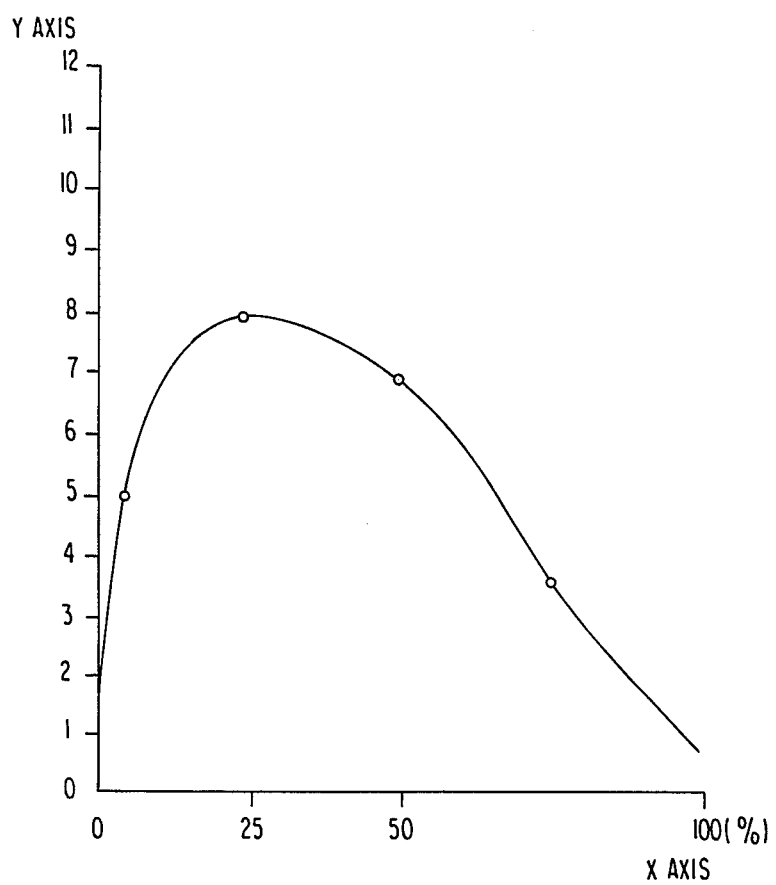

METHOD FOR PERCUTANEOUSLY ADMINISTERING PHYSIOLOGICALLY ACTIVE AGENTS

BACKGROUND OF THE INVENTION

Cross-Reference to Related Application

This application is a continuation-in-part of U.S. Ser. No. 729,023 filed Apr. 30, 1985, which in turn is a continuation of U.S. Ser. No. 496,732 filed May 20, 1983, both entitled "METHOD FOR PERCUTANEOUSLY ADMINISTERING PHYSIOLOGICALLY ACTIVE AGENTS", and both filed in the names of Heller et al, both abandoned.

FIELD OF THE INVENTION

The present invention relates to a method for accelerating the percutaneous absorption of a physiologically active agent (hereafter often merely an "active agent" for brevity).

DESCRIPTION OF THE PRIOR ART

Active agents are commonly administered to the skin or mucosal tissues to treat local problems and systemic administration of active agents is commonly accomplished by ingesting pills or by injections. However, recently attempts have been made to achieve systemic administration of active agents by topical applications to the skin or mucosal tissues. Such topical means of achieving systemic administration has the advantage that desired blood levels can be readily achieved and maintained so that duration of therapy can be readily controlled. Thus, side effects due to an overdose of the active agent can be prevented. Also, metabolism due to a first pass through the liver and gastric disturbances, which are characteristic of certain drugs such as indomethacin when administered orally, can also be eliminated.

However, normal skin is relatively impermeable to most therapeutic agents in that desired blood levels of the therapeutic agent cannot be achieved by means of percutaneous absorption. The percutaneous absorption of thereaputic agents can, however, be enhanced by means of adjuvants or penetration enhancers.

One of the best known of such penetrating adjuvants is dimethyl sulfoxide, the use of which is described in detail in U.S. Pat. No. 3,551,554 Herschler et al, which patent broadly suggests the use of dimethyl sulfoxide as a penetrating adjuvant for psychopharmocological drugs such as benzodiazepine derivatives.

British Pat. No. 1,504,302 Brooker et al deals with sedative methods and compositions and discloses the administration of sedatives by applying to the skin of a non-human animal a sedating amount of one or more sedative compounds in various penetrating adjuvants such as hydrocarbons such as aromatic hydrocarbons or paraffins, halogenated aliphatic hydrocarbons, ketones, esters, ethers, alcohols, amides or sulfones. Brooker et al broadly indicates that one or more of the above liquids can be used in combination, but exemplify the halogenated aliphatic hydrocarbons only with carbon tetrachloride and exemplify the amides only with dimethylformamide.

Japanese Patent Application No. 52-148,614 (unexamined) Yonemushi discloses, without supporting data or explanation of substance, the use of sulfones by-produced in the refining of petroleum "as solvents to enhance the efficacy of drugs for skin disease" and "as drug penetration enhancers".

U.S. Pat. No. 4,202,888 Eckert et al discloses absorbable pharmaceutical compositions comprising at least one cardiac glycoside distributed in a vehicle comprising an absorption-enhancing amount of at least a partial glyceride of a fatty acid of medium chain length.

U.S. Pat. No. 3,472,931 Stoughton relates to percutaneous absorption using lower alkyl amides, and exemplifies binary systems which comprise dimethylacetamide and ethanol, dimethylacetamide and isopropyl alcohol and dimethylacetamide and isopropyl palmitate. Stoughton does not exemplify nor disclose the combination of dimethylacetamide with higher molecular weight alcohols or higher molecular weight esters.

U.S. Pat. No. 4,017,641 DiGiulio deals with skin moisturizing compositions comprising 2-pyrrolidones which can be used with suitable oils and waxes including aliphatic straight chain fatty acids and alcohols of from about 10 to about 20 carbon atoms. This patent does not, however, deal with percutaneous administration of physiologically active agents.

European Patent Application No. 0043738 discloses binary percutaneous administration systems which comprise a monoglyceride, a diol or a diol ether in combination with a second component such as an alcohol, ester, amide or the like.

The present invention involves multicomponent carrier systems for the percutaneous administration of physiologically active agents which differ from the systems disclosed in the above prior art.

SUMMARY OF THE INVENTION

Per the present invention, it has been discovered that certain multicomponent carrier systems provide enhanced percutaneous administration of physiologically active agents (often merely referred to as "active agents" for brevity).

The carrier systems of the present invention comprise at least one conditioner (Component A) and at least one promoter (Component B).

The conditioners of the present invention are selected from aliphatic hydrocarbons or halogen substituted aliphatic hydrocarbons, alcohol esters of aliphatic carboxylic acids, mono- or di-ethers, ketones, or mixtures thereof.

The promoters of the present invention are selected from thioglycerols, lactic acid or esters thereof, cyclic ureas, compounds represented by the general formula $R_1R_2NCONR_3R_4$, pyrrolidone-type compounds, amides, lactones or mixtures thereof.

Per the present invention, a physiologically active agent can be percutaneously administered by blending the same with a combination of Component A and Component B and applying the same to the skin.

The above-described compositions can be used as bases for medical preparations comprising active agents applicable to the outer skin.

One object of the present invention is to provide base compositions or percutaneous absorption enhancing combinations (often abbreviated as PAEC and PAECs hereafter) for medical preparations for external use which enhance the permeability of active agents through the skin and the percutaneous absorption of active agents.

A second object of the present invention is to provide pharmaceutical compositions comprising a PAEC for external use which provides good permeability of active agents through the skin and percutaneous absorption of active agents.

A third object of the present invention is to provide a method for enhancing the permeability of active agents through the skin and percutaneous absorption of active agents using a PAEC per the present invention.

In a preferred embodiment, the combination of the present invention which enhances percutaneous absorption comprises one or more members selected from the group consisting of certain pyrrolidone-type compounds and amides and mixtures thereof and one or more members selected from the group consisting of certain alkyl halides, fatty acid esters, hydrocarbons and mixtures thereof.

A fourth object of the present invention is to provide PAECs which ensure rapid transepidermal delivery of physiologically active agents in man or other animals.

A fifth object of the present invention is to provide such rapid transepidermal delivery which provides drug blood levels in the therapeutic range for the treatment of humans and other animals.

A sixth object of the present invention is to provide, through transepidermal delivery, at appropriately adjusted rates, relatively constant therapeutic blood levels so as to avoid the side effects and reduced therapeutic effects that may result from wide fluctuations in blood levels over time.

BRIEF DESCRIPTION OF THE DRAWING

The FIGURE shows the transdermal penetration rate of an active agent with compositions having varying ratios of component A and component B (see Example 24).

DESCRIPTION OF PREFERRED EMBODIMENTS

Examples of component A include the following compounds.

(1) Straight, branched or cyclic aliphatic hydrocarbons having 5 to 24 carbon atoms which may be substituted with one or more halogens:

As halogen substituents, bromine and chlorine are preferred.

Straight or branched hydrocarbons having 5 to 24 (preferably 6 to 18) carbon atoms can be used which may be saturated or unsaturated with preferably 1 to 2 unsaturated bonds. In the case of cyclic hydrocarbons, 6 to 10 membered mono- or 10 to 12 membered dicyclic hydrocarbons are preferred and such may be substituted with saturated or unsaturated alkyl groups having 1 to 4 carbon atoms such as methyl, butyl, isopropenyl, etc.

Specific examples include n-pentane, n-hexane, n-heptane, n-octane, n-nonane, n-decane, n-undecane, n-dodecane, n-tetradecane, n-hexadecane, n-octadecane, 2-methylpentane, 2-methylhexane, 2,3-dimethylhexane, 2-methylnonane, 2,6-dimethyloctane, 2,2,4,4,6,8,8-heptamethylnonane, pristane, limonene, hydrogenated limonene dimer, cyclohexane, 1,3-dimethylcyclohexane, cyclooctane, isobutyl-cyclohexane, cyclododecane, methyldecaline, decaline, octyl chloride, decyl chloride, dodecyl chloride, hexadecyl chloride, dodecyl bromide, dichlorododecane, etc.

(2) Alcohol esters of aliphatic carboxylic acids having a total number of carbon atoms of from 7 to 18, preferably 7 to 17;

As the alcohol moiety, monovalent alcohols having 1 to 6 carbon atoms such as methyl alcohol, ethyl alcohol, n-propyl alcohol, iso-propyl alcohol, n-butyl alcohol, iso-butyl alcohol, sec-butyl alcohol, t-butyl alcohol, n-amyl alcohol, iso-amyl alcohol, n-hexyl alcohol, etc., are preferred. Further, as the carboxylic acid moiety, fatty acids having 6 to 16 carbon atoms are preferred and saturated fatty acids having 8 to 14 carbon atoms are most preferred. Specific examples of such esters include methyl laurate, ethyl laurate, butyl laurate, isopropyl myristate, etc.

(3) Mono- or di-ethers having 10 to 18 carbon atoms:

Specifically, there are alkyl monoethers such as dihexyl ether, dioctyl ether, methoxydodecane, ethoxydodecane, etc., ethers having an alicyclic group such as 1,8-cineole, etc., alkyl diethers such as ethylene glycol dibutyl ether, ethylene glycol dioctyl ether, etc.

(4) Ketones having 10 to 18 carbon atoms:

Aliphatic ketones are preferred, examples of which include 2-undecanone, 3-undecanone, 4-undecanone, 5-undecanone, 6-undecanone, 2-dodecanone, 4-dodecanone, 5-dodecanone, 2-tridecanone, 3-tridecanone, 7-tridecanone, 8-pentadecanone, etc.

Examples of component B include the following compounds:

(1) Thioglycerols:

Any mono-, di- and trithioglycerols can be used, an example of which includes α-monothioglycerol.

(2) Lactic acid and esters thereof:

As the alcohol moiety in the esters, monovalent aliphatic alcohols having 1 to 4 carbon atoms are preferred, specific examples of which include lactic acid, methyl lactate, ethyl lactate, butyl lactate, etc.

(3) Cyclic ureas:

5-Membered or 6-membered rings are preferred, specific examples of which include N,N'-dimethyleneurea, N,N'-diethylethylene urea and the corresponding propylene ureas, etc.

(4) Compounds represented by the general formula:

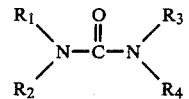

wherein $R_1$, $R_2$, $R_3$ and $R_4$ each represents a hydrogen atom, a lower alkyl group having 1 to 4 carbon atoms (methyl, ethyl, n-propyl, iso-propyl, n-butyl, etc.) or an acyl group having 1 or 2 carbon atoms:

Specific examples thereof include urea, N-methylurea, N-ethylurea, N-butylurea, 1,1-dimethylurea, 1,3-dimethylurea, 1,1,3,3-tetramethylurea, N-acetyl-N'-methylurea, etc.

(5) Compounds represented by the general formula:

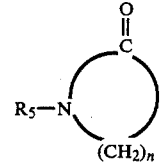

wherein $R_5$ represents a hydrogen atom or a lower alkyl group having 1 to 4 carbon atoms (methyl, ethyl, n-propyl, iso-propyl, etc.) and n represents an integer of 3 to 5:

Specific examples thereof include 2-pyrrolidone, N-methyl-pyrrolidone, N-methylpiperidone, caprolactam, N-methylcaprolactam, etc.

(6) Compounds represented by the general formula:

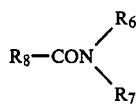

wherein $R_6$ represents a hydrogen atom or an alkyl group having 1 to 3 carbon atoms (methyl, ethyl, n-propyl, etc.) and $R_7$ and $R_8$ each represents an alkyl group having 1 to 3 carbon atoms, with the proviso that $R_6$, $R_7$ and $R_8$ have in total at least 3 carbon atoms:

Specific examples thereof include N,N-diethyl formamide, N,N-dimethylacetamide, N,N-diethylacetamide, N,N-dimethylpropionamide, N,N-diethylpropionamide, etc.

(7) Lactones having 4 to 6 carbon atoms:

Specific examples thereof include γ-butyrolactone, δ-valerolactone, etc.

In addition to the above, there are certain most preferred PAECs per the present invention, and these are discussed below.

We are unsure why the most preferred combination of PAECs of the present invention offers enhanced percutaneous absorption; however, the data we have generated indicate that there is a synergistic effect between the two groups of materials.

We consider the materials such as pyrrolidone-type compounds and amides to basically serve a promoter function and materials such as the alkyl halides, fatty acid esters, and hydrocarbons to serve as conditioners which enhance the function of the promoter. We further believe that the promoters carry the active agent whereas the conditioners open up the stratum corneum. We do not wish to be bound by these theories, and we merely use the terminology "promoter" and "conditioner" to maintain a line of distinction between the two classes of materials which are mandatorily used in combination.

The most preferred conditioners as component A of the present invention include one or more members selected from the group consisting of alkyl halides, fatty acid esters, hydrocarbons and mixtures thereof.

Of the alkyl halides, those having from 8 to 16 carbon atoms are most preferred, with chloride being the preferred halogen. Both alkyl bromides and iodides are potentially useful, but alkyl bromides and alkyl iodides tend to be unstable. Alkyl fluorides are also useful.

The alkyl moiety may be straight or branched chain, may be aliphatic, cycloaliphatic or unsaturated, e.g., alkanes and alkenes are useful.

Most preferred alkyl halides are later exemplified.

The hydrocarbons most preferably have 10 to 18 carbon atoms. They may be straight or branched chain and may be aliphatic, cycloaliphatic or unsaturated, e.g., alkanes and alkenes are useful.

The fatty acid esters are conveniently represented by the formula $R_1COOR_2$, $R_1$ representing the acid moiety and $R_2$ representing the alcohol moiety. It is most preferred that the total number of carbon atoms in $R_1$ and $R_2$ be from 10 to 17.

$R_1$ and $R_2$ may be linear, branched, saturated, unsaturated, or aromatic.

The most preferred promoters as component B include the pyrrolidone-type compounds and the amides.

The pyrrolidones are most preferably alkyl pyrrolidones of the formula:

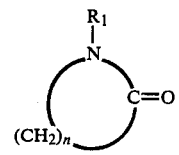

where $R_1$ is an alkyl group containing up to 4 carbon atoms and n is 3 to 5.

The amides are most preferably represented by the formula:

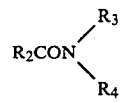

where $R_2$ can be hydrogen or an alkyl group with up to 3 carbon atoms and $R_3$ and $R_4$ can be an aliphatic group with up to 3 carbon atoms.

The base compositions of the present invention can be prepared by homogenously dissolving component A in component B. The amount of component A to be used is generally from 0.1 to 80% by weight based on the total weight of components A and B, preferably 0.5 to 50% by weight. Of course, pharmaceutically acceptable additives such as water, etc., can also be added to the base compositions.

The pharmaceutical compositions for topical application per the present invention can be prepared by blending active agents with the above-described base compositions. There is no particular limit on the active agents used so long as the active agents are systemically active and percutaneously applicable.

Specific examples of active agents include benzodiazepines (e.g., Diazepam, Nitrazepam, Flunitrazepam, Lorazepam, Fludiazepam, Clonazepam), diuretic agents [e.g., thiazides (e.g., Bendroflumethiazide, Polythiazide, Methyclothiazide, Trichloromethiazide, Cyclopenthiazide, Bentylhydrochlorothiazide, Hydrochlorothiazide, Bumetanide)], antihypertensive agents (e.g., Clonidine), antihistamic agents [e.g., aminoethers (e.g., diphenhydramine, Carbinoxamine, Diphenylpyraline), ethylenediamines (e.g., Fenbenzamine), monoamines (e.g., Chlorophenylamines)], non-steroid antiinflammatory agents (e.g., Indomethacine, Ibuprofen, Ibufenac, Alclofenac, Diclofenac, Mefenamic acid, Flurbiprofen, Flufenamic acid, Ketoprofen), anti-tumor agents (e.g., 5-fluorouracil, 1-(2-tetrahydrofuryl)-5-fluorouracil, Cytarabine, Floxuridine). Steroid antiinflammatory agents (e.g., Cortisone, Hydrocortisone, Prednisolone, Predonisone, Triamcinolone, Dexamethasone, Betamethasone), antiepileptic agents (e.g., Ethosuximide), antiarrythmic agents (e.g., Ajmalin, Purajmalin. Pindolol, Propranolol, Quinidine), psychotropic agents [e.g., Clofluperol, Trifluperidol, Haloperidol, Moperone), scopolamines (e.g., methyl scopolamine, butyl scopolamine), metoclopramide, chlorpromazine, atropines (e.g., methyl atropine bromide, methylanisotropine bromide), vascular dilating agents (e.g., isosorbide dinitrate, nitroglycerine, pentaerythritol tetranitrate, propanyl nitrate, dipyridamole), antibiotics, e.g., tetracyclines (e.g., Tetracycline, Oxytetracycline, metacycline, doxycycline, Minocycline), chloramphenicols, erythromycines], etc. The method of the present invention can also be utilized to percutaneously administer peptides such as LH-RH, insulin and the like. Of course, pharmaceutically acceptable salts such as the hydrochloride, sodium chloride, potassium, hydrogen bromide, etc., salts can be used.

Since the present invention is of particular application with respect to the benzodiazepine materials, these are discussed in more detail below. Particularly preferred benzodiazepine materials are those which illustrate the benzodiazepine skeleton as schematically illustrated as follows:

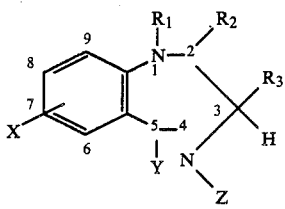

wherein X is Cl, Br, or NO₂ and Y is

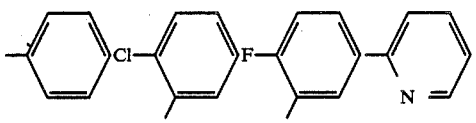

with varying degrees of unsaturation and substitution at positions 1, 2, 3, 4, and 5 as follows:

(a) 1, 2 and 4, 5 are unsaturated: $R_1$ and $R_3$ are H; $R_2$ is

($R$ is H or CH₃) and N—Z is N→O.

(b) 1, 2 are saturated and 4, 5 are unsaturated: $R_3$ is H or OH; —$R_2$ is —H or =O or =N*; $R_1$ is

($R$ is H, CH₃ or

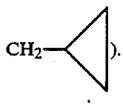

).

or CH₂—CH₂—N(C₂H₅)₂ or $R_1$ is C(R)=N* ($R$ is H or CH₃) and is joined to $R_2$ via "*" (a single bond) as follows:

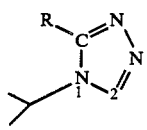

(c) 1, 2 and 4, 5 are saturated: $R_1$ is H; —$R_2$ is =O; $R_3$ is H and positions 4 and 5 constitute a second ring system as follows:

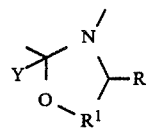

where R and R¹ are H and CH₃.

Specific examples of benzodiazepines which can be percutaneously administered using the active ingredient/penetration adjuvant combinations of the present invention include:

(a) Chlordiazepoxide; 7-Chloro-2-methylamino-5-phenyl-3H-1,4-benzodiazepine-4-oxide (b) Diazepam; 7-Chloro-1,3-dihydro-1-methyl-5-phenyl-2H-1,4-benzodiazepine-2-one (c) Oxazepam; 7-Chloro-1,3-dihydro-3-hydroxy-5-phenyl-2H-1,4-benzodiazepine-2-one (d) Temazepam; 7-Chloro-1,3-dihydro-3-hydroxy-1-methyl-5-2H-1,4-benzodiazepine-2-one (e) Lorazepam; 7-Chloro-5-(o-chlorophenyl)-1,3-dihydro-3-hydroxy-2H-1,4-benzodiazepine-2-one (f) Prazepam; 7-Chloro-1-cyclopropylmethyl-1,3-dihydro-5-phenyl-2H-1,4-benzodiazepine-2-one (g) Fludiazepam; 7-Chloro-1,3-dihydro-5-(2-fluorophenyl)-1-methyl-2H-1,4-benzodiazepine-2-one (h) Flurazepam; 7-Chloro-1-(2-(dimethylamino)ethyl)-5-(o-fluorophenyl)-1,3-dihydro-2H-1,4-benzodiazepine-2-one (i) Medazepam; 7-Chloro-2,3-dihydro-1-methyl-5-phenyl-1H-5,4-benzodiazepine (j) Bromazepam; 7-Bromo-5-(2-pyridyl)-3H-1,4-benzodiazepine-2(1H)-one (k) Nitrazepam; 1,3-Dihydro-7-nitro-5-phenyl-2H-1,4-benzodiazepine-2-one (l) Nimetazepam; 1-Methyl-7-nitro-5-phenyl-1,3-dihydro-2H-1,4-benzodiazepine-2-one (m) Clonazepam; 5-(o-Chlorophenyl)-7-nitro-1H-1,4-benzodiazepine-2(3H)-one (n) Flunitrazepam; 5-(o-Fluorophenyl)-1,3-dihydro-1-methyl-7-nitro-2H-1,4-benzodiazepine-2-one (o) Estazolam; 8-Chloro-1,6-phenyl-4H-s-triazolo(4,3-)(1,4)-benzodiazepine (p) Triazolam; 8-Chloro-6-(o-chlorophenyl)-1-methyl-4H-s-triazolo(4,3-)(1,4)-benzodiazepine (q) Alprazolam; 8-Chloro-1-methyl-6-phenyl-4H-s-triazolo(4,3-)(1,4)-benzodiazepine (r) Oxazolam; 10-Chloro-2,3,5,6,7,11b-hexahydro-2-methyl-11b-phenylbenzo(6,7)-1,4-diazepino(5,4-b-oxazol-6-one (s) Cloxazolam; 10-Chloro-11b-(o-chlorophenyl)-2,3,5,6,7,11b-hexahydrobenzo(6,7)-1,4-diazepino(5,4-b)oxazol-6-one (t) Haloxazolam; 10-Bromo-11b-(o-fluorophenyl)-2,3,7,11b-tetrahydro-oxazolo(3,2,-d)(1,4)benzodiazepine-6(5H)-one Especially preferred are benzodiazepines (b), (e), (i), (k), (l), (n) and (o).

The amount of active agent(s) blended is sufficient if it is effective for achieving the desired pharmaceutical effect, which varies depending upon the kind of active agents, body weight of the patient, symptoms, etc. The amount may thus be suitably chosen depending upon these conditions. In general, it is preferred that active agents be employed in an amount of 0.01 to 50% by weight, more preferably 0.05 to 10% by weight, based on the total amount of the PAEC comprising component A and component B.

The dose of the active agents administered can be controlled by increasing or decreasing the area of skin to which the pharmaceutical compositions are applied. Accordingly, the amount of the active agent is not necessarily limited to the above-described ones.

As will be apparent to one skilled in the art, with increasing concentrations of active agent increasing amounts of active agent will be absorbed by the subject. The following discussion is given in terms of blood levels of drug (ng/ml of plasma), this being dependent upon the total area of dermal application, as there is a substantially linear increase in amount of active agent absorbed with area.

For a constant area of application and a constant absolute amount of adjuvant, the blood level of active agent at any given time is a function of the concentration of active agent in the composition. That is, increased concentrations of active agent in the formulation result in more rapid active agent penetration and higher blood levels.

A further factor which must be considered is that the amount of active agent absorbed will depend on the site of application, for example, scalp, ventral forearm, behind the ear, chest, etc. Typically an area rich in blood vessels is selected.

For most applications, the concentration of active agent in the PAEC will generally be on the order of 0.01 to 50%, the amount of PAEC applied will be about 0.1 mg to 100 mg per $cm^2$ and the total area of application will be on the order of about 0.5 $cm^2$ to about 10 $cm^2$, which will provide therapeutic blood levels of the desired active agent.

These ranges are not, however, to be considered as limitative.

In general, the rate of transepidermal active agent absorption will approach the rate of oral absorption depending upon the factors previously discussed (nature and amount of PAEC, concentration of active agent in the formulation, and surface area of skin application). Thus, peak blood levels of the active agent may be reached more slowly or at about the same rate and will reach about the same level as those obtained by oral administration. Alternatively, the blood level of active agent attained by single dose oral administration may be maintained for an extended period by subsequent percutaneous administration of the active agent. In the latter case, the initial oral dose may be smaller than the normal therapeutic oral dose so that side effects associated with higher-than-minimal therapeutic blood levels attained by a reduced oral dose may be maintained by the subsequent transepideraml administration at a proper rate.

Therapeutic oral doses of diazepam in man produce blood levels of approximately 100 ng/ml plasma [S. A. Kaplan, M. L. Jack, K. Alexander, R. E. Weinfield, J. Pharm. Sci., 62, 1789-1796 (1973)]. Such a blood level is easily attainable by percutaneous administration by way of the present invention and produces pharmacological (behavioral) signs of therapeutic effectiveness in appropriate animal models for man, e.g., the rhesus monkey.

The method of the present invention finds application with mammals in general, most particularly man and domestic animals such as cows, sheep, horses, dogs, cats and the like.

The pharmaceutical composition of the present invention is administered to the outer skin as a simple mixture or as a medical preparation by adding known pharmaceutically acceptable third components in the form of solutions, ointments (paste-including creams and gels) lotions, adhesive tapes, a plaster, etc.

For example, solutions may simply comprise the active agent dissolved in the PAEC with optional components, e.g., glycerin, and the solutions may be incorporated into absorbents, e.g., a gauze, porous membrane, etc.

Ointments, gels or creams may contain conventional ingredients (e.g., polyethylene glycol and hydroxy propylcellulose, etc.) to form the same, and the same may be spread onto backing materials, e.g., a plastic film.

Similarly, plasters or adhesives tapes may contain the active agent and PAEC in an adhesive base, e.g., acrylic copolymers or other synthetic gums.

The PAEC may be added to such a composition in varying amounts as desired, generally from 10 to 99% by weight.

In developing the present invention, we have used both diffusion cells and an animal model. The diffusion cell methods provided a qualitative assessment of the active agent/PEAC effect on percutaneous absorption and the animal model (rhesus monkey) test provided the most acceptable pharmacokinetic model for man as indicated in J. Soc. Cosmet. Chem., 30, 297-307. Sept./Oct. 1979 and Toxicol. Appl. Pharmacol., 32, 394-398, 1975.

In Vitro Skin Penetration Studies with Diffusion Cell Technique

Rat full thickness skins were used in the following two types of diffusion cell methods.

The skin was excised from the shaved abdominal site of deceased male albino rats weighing 250~300 g, and washed with normal saline solution after the subcutaneous fat was carefully removed with scissors.

In examples 1 to 34 and 37, the finite dose technique of Franz, Curr. Probl. Dermatol., Vol. 7, p. 58~68 (Karger, Basel, 1978) was followed. The rat skin was mounted horizontally in a diffusion cell apparatus; the exposed area of the skin approximated 0.7 $cm^2$.

The active agent/PEAC solution of known concentration was added to the upper compartment of the cell, which was exposed to the epithelial side of the skin and a normal saline solution was placed in the lower compartment.

The penetration rate was studied in a thermostated bath at 30° C. At appropriate intervals samples were withdrawn from the lower compartment and subsequently analyzed for active agent concentration by standard analytical methods.

In examples 35 and 36, transdermal penetration effects were analyzed following the method of Michaels, AIChE Journal, 21 [5], 985-996, 1975. The rat skin was mounted in the diffusion cell in a vertical position between the upstream and the downstream compartments; the exposed area of the skin approximated 4.15 $cm^2$.

The active agent/PEAC solution of known concentration was added to the upstream compartment to which the epithelial side of the skin was exposed, and a normal saline solution was added to the downstream compartment.

In Vivo Rhesus Monkey Test

Male rhesus monkeys weighing 10-14 Kg each were used as the subject. An appropriate area of the monkey's chest was shaved 24 hours before drug application.

Drug formulations comprising the PEAC were applied to a certain area of the chest as indicated in each example. The monkey was restrained in a chair to prevent it from touching its chest.

Blood samples were taken at appropriate intervals after the application. The heparinized blood was centrifuged, and the plasma was removed and stored at −20° C. until analyzed.

Diazepam in plasma was analyzed following the GLC method of Aingales, J. Chromatog., 75, 55–78, 1973, unless otherwise indicated.

The results are set forth in the following Examples.

Hereafter the present invention will be illustrated with reference to the examples and experiments in more detail, but it is not to be deemed to be limited thereto.

EXAMPLES 1 TO 23

[Basic Formulation]

| | | |
|---|---|---|
| (1) | Diazepam | 3 g |
| (2) | Component B | 72 g |
| (3) | Component A | 25 g |

Liquid compositions having the above-described basic formulation were prepared using the components shown in Table 1 as (2) and (3), respectively, by firstly mixing (3) with (2) and then dissolving (1) in the mixture. In the case that component B was a solid at ambient temperature or was not homogenously mixed with component A, 20 wt.% of ethylene glycol monobutyl ether based on the weight of components A and B was used as an agent for assisting dissolution (in this case, a * mark is attached in Table 1).

CONTROL FORMULATION 1

| | | |
|---|---|---|
| (1) | Diazepam | 3 g |
| (2) | Component B | 97 g |

The 23 examples of Control Formulation 1 thus obtained were used to calculate the Q values later described.

Compositions were obtained using only component B described in Table 1, respectively, by dissolving (1) in (2) wherein Component A was not present in the Examples.

COMPARATIVE EXAMPLES 1 AND 2

| | | |
|---|---|---|
| (1) | Diazepam | 3 g |
| (2) | Polar compound | 72 g |
| (3) | Component A | 25 g |

The compositions described above were prepared using component A and a compound (see Table 2) outside the present invention, in accordance with the procedures of Examples 1 to 23.

COMPARATIVE EXAMPLES 3 AND 4

| | | |
|---|---|---|
| (1) | Diazepam | 3 g |
| (2) | Component B | 72 g |
| (3) | Non-polar compound | 25 g |

The compositions described above were obtained using component B and a compound (see Table 3) outside the present invention, in accordance with the procedures of Examples 1 to 23.

The amount of transport of the active agent in the compositions obtained in Examples 1 to 23, Control Formulation 1 and Comparative Examples 1 to 4 through the rat skin was measured as earlier described. The results are shown in Table 1, Table 2 and Table 3.

In Table 1, Table 2 and Table 3, the Q value has the following meaning:

$$C/D = Q$$

C: Transport of active agent through the skin in the Examples and the Comparative Examples.

D: Permeation amount of active agent through the skin in Control Formulation 1.

TABLE 1

| Example No. | Component B | Component A | Q Value |
|---|---|---|---|
| 1* | methyl lactate | hexane | 3.4 |
| 2* | methyl lactate | dodecane | 4.0 |
| 3* | methyl lactate | dodecyl bromide | 22.0 |
| 4 | methyl lactate | isopropyl myristate | 4.8 |
| 5* | methyl lactate | dihexyl ether | 12.4 |
| 6 | methyl lactate | 2-dodecanone | 2.6 |
| 7* | ethyl lactate | dodecane | 2.9 |
| 8 | ethyl lactate | isopropyl myristate | 4.9 |
| 9 | butyl lactate | dodecane | 2.2 |
| 10* | α-thioglycerol | isopropyl myristate | 9.0 |
| 11 | N,N—dimethyl ethylene urea | dodecane | 5.3 |
| 12 | N,N'dimethyl ethylene urea | isopropyl myristate | 8.5 |
| 13* | propylene urea | isopropyl myristate | 4.7 |
| 14* | 1,3-dimethyl urea | isopropyl myristate | 4.2 |
| 15 | 1,1,3,3-tetramethyl urea | isopropyl myristate | 10.7 |
| 16* | 2-pyrrolidone | isopropyl myristate | 9.2 |
| 17 | N—methyl-2-pyrrolidone | isopropyl myristate | 14.2 |
| 18 | N—methyl-2-piperidone | isopropyl myristate | 13.2 |
| 19 | N—methyl-ε-caprolactam | isopropyl myristate | 11.5 |
| 20 | N,N—dimethyl acetamide | isopropyl myristate | 13.8 |
| 21 | N,N—diethyl acetamide | isopropyl myristate | 12.2 |
| 22 | N,N—dimethyl propionamide | isopropyl myristate | 12.9 |
| 23 | γ-butyrolactone | isopropyl myristate | 4.9 |

TABLE 2

| Comparative Example No. | Component B | Component A (false) | Q Value |
|---|---|---|---|
| 1 | N—methyl-2-pyrrolidone | tetraethylene glycol | 0.9 |
| 2 | N—methyl-2-pyrrolidone | ethyl alcohol | 1.1 |

TABLE 3

| Comparative Example No. | Component B (false) | Component A | Q Value |
|---|---|---|---|
| 3 | glycerin triacetate | isopropyl myristate | 0.6 |
| 4 | N,N—diethyl toluamide | isopropyl myristate | 1.4 |

EXAMPLE 24

| | | |
|---|---|---|
| (1) | Diazepam | 3% |

| | |
|---|---|
| (2) Component B | 0-100 g |
| (3) Component A | 100-0 g |

Compositions were prepared by dissolving 3 g of diazepam in 100 g mixtures of component B and component A prepared by varying the mixing ratio (weight ratio) from 100:0 to 0:100. With the respective compositions thus obtained, the skin permeation rate of diazepam for 8 hours was measured and the results are shown in FIG. 1. In FIG. 1, the y-axis indicates relative values of the permeation rates of each of the compositions to the permeation rate of the active agent with the composition comprising component B alone and the x-axis indicates the % by weight of component B to the total weight of component A and component B. Component B was N,N,N',N'-tetramethyl urea and component A was isopropyl myristate.

EXAMPLES 25-34

| | (Basic Composition A) | |
|---|---|---|
| (1) | active agent | 3 g |
| (2) | 25 volume % isopropyl myristate in dimethyl propionamide (based on total volume | 97 g |
| | (Comparative Composition B) | |
| (1) | active agent | 3 g |
| (2) | dimethyl propionamide | 97 g |
| | (Comparative Composition C) | |
| (1) | active agent | 3 g |
| (2) | acetone | 97 g |

The above compositions of various active agents shown in Table 4 were prepared and the flux rate of the active agent was measured. The results are shown in Table 4.

TABLE 4

| Example No. | Active Agent | Composition A | B | C |
|---|---|---|---|---|
| | | Flux($\mu$g/cm$^2$/24 hrs) | | |
| 25 | tetracycline | 2157 | 355 | 0 |
| 26 | chloramphenicol | 272 | 182 | 8 |
| 27 | scopolamine (free base) | 3039 | 1596 | 685 |
| 28 | haloperidol | 327 | 357 | 22 |
| 29 | bendroflumethiazide | 92 | 26 | 0 |
| 30 | chlorpheniramine maleate | 1091 | 329 | 348 |
| 31 | ibuprofen | 1085 | 835 | 242 |
| 32 | dichlofenac sodium | 829 | 588 | 28 |
| 33 | flufenamic acid | 598 | 311 | 26 |
| 34 | indomethacine | 394 | 150 | 30 |

NOTE:
in the case of formulation C, the upper compartment of the diffusion cell was open to the air and the acetone was evaporated off.

Further, in the following examples, the abbreviations below are used:
EtOH—ethanol
C$_{12}$Cl—n-dodecyl chloride
iPrM—isopropyl myristate
DMAc—dimethyl acetamide
MP—methyl pyrolidone Unless otherwise indicated, in all of the following examples the active agent is diazepam, diazepam flux is given in terms of $\mu$g/cm$^2$/8 hours, 25 volume percent component B with respect to component A and component B volume was used in the composition and 2.5 weight percent diazepam was used. For purposes of comparison, in certain instances the results for solvents alone and adjuvants alone are given.

EXAMPLE 35

This example shows the use of an alkyl halide as component A in combination with a pyrrolidone or an amide as component B.

All results are in terms of diazepam flux rate for 8 hours through the skin.

The flux values for 8 hours are shown in Table 5.

TABLE 5

| Component B | Component A | Diazepam Flux ($\mu$g/cm$^2$/8 hrs) |
|---|---|---|
| N—methyl-2-pyrrolidone | — | 94 |
| N,N—dimethyl acetamide | — | 139 |
| — | 1-chlorododecane | 40 |
| N—methyl-2-pyrrolidone | 1-chlorododecane | 849 |
| N,N—dimethyl acetamide | 1-chlorododecane | 887 |

EXAMPLE 36

This example shows the use of pyrrolidones as component B and a fatty acid ester as component A for the present invention.

With isopropyl myristate alone the diazepam flux was 29. With N-methyl pyrrolidone alone the flux was 94. For 25% iPrM in MP, the flux was 530.

Again, the synergistic effect of the PAEC of the present invention is easily seen.

Also, for nitrazepam, a type of benzodiazapine as is diazepam, a flux of 524 was obtained with 25% iPrM in MP.

Table 6 shows the relative diazepam flux with lower concentrations of iPrM in MP compared to the flux with 25% iPrM in MP. Also Table 9 shows substantially greater flux for a higher N-alkyl derivative of a 2-pyrrolidone, N-ethyl-2-pyrrolidone, as opposed to N-methyl-2-pyrrolidone.

TABLE 6

| | Relative Flux |
|---|---|
| 25% iPrM in MP | as 1 |
| 10% iPrM in MP | 1.0 |
| 5% iPrM in MP | 1.0 |
| 1% iPrM in MP | 0.5 |
| 25% iPrM in N—ethyl-2-pyrrolidone | 1.5 |

EXAMPLE 37

This example shows the use of fatty acid esters as component A and amides as component B.

For 25% iPrM in DMAc, the diazepam flux was 749.

Table 10 shows the relative flux of 25% various fatty acid esters in various amides to 25% iPrM in DMAc. Also, as a comparison, the relative flux of combinations, at least one of which was outside of this invention, to 25% iPrM in DMAc is shown in Table 7.

TABLE 7

| Formulations | Relative Flux |
|---|---|
| 25% methyl caprylate in DMAc | 1.0 |
| 25% methyl laurate in DMAc | 1.4 |
| 25% isopropyl myristate in DMAc | as 1.0 |
| 25% ethyl palmitate in DMAc | 0.50 |
| 25% (isopropyl palmitate) in DMAc | 0.35 |
| 25% (ethyl stearate) in DMAc | 0.15 |
| 25% isopropyl myristate in diethyl formamide | 1.1 |
| | 1.1 |
| 25% isopropyl myristate in DMAc | as 1.0 |

TABLE 7-continued

| Formulations | Relative Flux |
| --- | --- |
| 25% isopropyl myristate in diethyl acetamide | 0.90 |
| 25% isopropyl myristate in dimethyl propionamide | 0.95 |
| 25% isopropyl myristate in (dimethyl formamide) | 0.60 |
| 25% isopropyl myristate in (methyl acetamide) | 0.10 |

Note:
Compounds in ( ) are outside of this invention.

EXAMPLE 38

This example shows in vivo plasma diazepam levels with a topical diazepam formulation using a combination of component A and component B per this invention.

150 mg of diazepam was dissolved in 6 ml of 25% $C_{12}Cl$ in MP. To this solution was added 1.2 g of polyvinyl pyrrolidone (Aldrich Chemical Co; Cat. 85, 647-9; molecular weight approx. 36,000). A viscose solution was obtained.

0.5 ml of the solution was placed in a polyester cup 4 $cm^2$ in diameter, 2 mm in depth and having a volume of 0.5 ml. The solution in the cup was placed on the monkey's chest and fixed thereto with adhesive. As a comparison, a 10 mg diazepam tablet (Valium ®; Roche) was given orally to the same monkey. The results are shown in Table 8.

TABLE 8

| Formulations | Diazepam Plasma Level (ng/ml of plasma) | | | |
| --- | --- | --- | --- | --- |
| | 1 hr | 3 hr | 5 hr | 7 hr |
| Topical Formulation | 34 | 42 | 37 | 30 |
| Oral Administration | 50 | — | 34 | — |

EXAMPLE 39

This example shows in vivo plasma diazepam levels with a topical gel formulation.

150 mg of diazepam was dissolved in 6 ml of 25% iPrM in N,N'-dimethyl ethylene urea. To this solution was added 120 mg of Klucel ® (cross-linked hydroxypropylcellulose type HF, Hercules Inc.) and the same stirred thoroughly to obtain a uniform gel.

1.0 ml of the gel was applied to 49 $cm^2$ of the chest area of the monkey; the applied area was left open to the air for the duration of the experiment. The result is shown in Table 9.

TABLE 9

| Formulations | Diazepam Plasma Level (ng/ml of plasma) | | | | |
| --- | --- | --- | --- | --- | --- |
| | 1 hr | 2 hr | 3 hr | 5 hr | 7 hr |
| Gel | 215 | 181 | 147 | 132 | 128 |

The following examples further illustrate the broad application of the promoter/conditioner combination of the present invention with various physiologically active agents.

In all instances the in vitro diffusion cell technique or the in vivo rhesus monkey test earlier described were used. In all instances analysis was by conventional HPLC (high pressure liquid chromatography). Details and citations are given for illustrative techniques.

All in vitro $\mu g/cm^2/hr$. values represent the average of three different diffusion cells for purposes of greater reliability.

In Examples 40 to 48, the finite dose techniquie of Franz earlier cited was followed; details are earlier given.

EXAMPLE 40

The physiologically active agent was Pindolol, a Beta-blocker, which has the formula:

$$O-CH_2-CH-CH_2-NH-CH\begin{matrix}CH_3\\CH_3\end{matrix}$$

The Pindolol vehicle combination was:

| IV. 25 mg Pindolol + 25% ethyl laurate in N—methyl pyrrolidone. | | | | |
| --- | --- | --- | --- | --- |
| 2 hrs. | 4 hrs. | 6 hrs. | 8 hrs. | ($\mu g/cm^2/hr$) |
| 204.9 | 222.6 | 62.0 | 43.6 | |

Detection was in a conventional manner via HPLC using a mobile phase of 70% A (0.5 acetic acid (v/v) with 1.0 g/l sodium pentane sulfonate) and 30% B (90% acetonitrile and 10% $H_2O$ (v/v) with 1.0 g/l sodium pentane sulfonate); the columnn was ASI $C_{18}$ 300×3.9 mm and the flow rate was 2 ml/min by UV at 267 nm.

EXAMPLE 41

The physiologically active agent was Propranolol (HCl), a commercially available Beta-blocker, which has the formula (free base):

$$O-CH_2-\overset{OH}{\underset{|}{CH}}-CH_2-NH-CH\begin{matrix}CH_3\\CH_3\end{matrix}$$

In the Table below, the following combinations were used:

I. 25 mg Propranolol+25% isopropyl myristate in N-methyl pyrrolidone

II. 25 mg Propranolol+25% isopropyl myristate in N-methyl piperidone

III. 25 mg Propranolol+25% isopropyl myristate in N-methyl caprolactam

IV. 25 mg Propranolol+25% ethyl laurate in N-methyl pyrrolidone

The results were:

| | 2 hrs. | 4 hrs. | 6 hrs. | 8 hrs. | ($\mu g/cm^2/hr$) |
| --- | --- | --- | --- | --- | --- |
| I. | 98.1 | 148.9 | 216.3 | 205.5 | |
| II. | 83.3 | 151.6 | 233.5 | 225.9 | |
| III. | 14.6 | 87.5 | 199.9 | 214.8 | |
| IV. | 123.4 | 220.8 | 316.6 | 263.3 | |

Illustrating one analysis procedure useful, i.e., HPLC, the mobile phase was 45% A (90% acetonitrile and 10% H₂O with 1.0 g/l of sodium pentane sulfone) and 55% B (0.5% acetic acid (v/v) with 1.0 g/l of sodium pentane sulfonate), the column was ASI C$_{18}$ 300×3.9 mm, the flow rate was 2 ml/min and detection was by UV at 292 nm.

EXAMPLE 42

The physiologically active agent was Indomethacin, a commercially available NSAID, which is 1-(p-chlorobenzoyl)-5-methoxy-2-methylindole-3-acetic acid.

In the Table below, the following combinations were used:

I. 25 mg Indomethicin+25% isopropyl myristate in N-methyl pyrrolidone
II. 25 mg Indomethicin+25% isopropyl myristate in N-methyl piperidone
III. 25 mg Indomethicin+25% isopropyl myristate in N-methyl caprolactam
IV. 25 mg Indomethicin+25% ethyl laurate in N-methyl pyrrolidone.

The results were:

|      | 2 hrs. | 4 hrs. | 6 hrs. | 8 hrs. | (μg/cm²/hr) |
|------|--------|--------|--------|--------|-------------|
| I.   | 65.1   | 39.0   | 21.5   | 13.2   |             |
| II.  | 55.7   | 49.3   | 29.3   | 15.1   |             |
| III. | 11.3   | 56.8   | 41.3   | 21.8   |             |
| IV.  | 89.5   | 63.7   | 23.0   | 13.9   |             |

Analysis was per the method of Cooper et al, *Journal of Chromatography*, 233, 289 (1982), modified to the column size of Example 40.

EXAMPLE 43

The physiologically active agent was Diclofenac, a commercially available NSAID which is sodium 2-(2,6-dichloroanilino)phenylacetate C$_{14}$H$_{10}$Cl$_2$NNAO$_2$=318.14.

In the Table below, the following combinations were used:

I. 25 mg Diclofenac+25% isopropyl myristate in N-methyl pyrrolidone
II. 25 mg Diclofenac+25% isopropyl myristate in N-methyl piperidone
III. 25 mg Diclofenac+25% isopropyl myristate in N-methyl caprolactam
IV. 25 mg Diclofenac+25% ethyl laurate in N-methyl pyrrolidone.

The results were:

|      | 2 hrs. | 4 hrs. | 6 hrs. | 8 hrs. | (μg/cm²/hr) |
|------|--------|--------|--------|--------|-------------|
| I    | 123.5  | 44.2   | 27.2   | 18.1   |             |
| II.  | 95.0   | 53.9   | 33.3   | 22.1   |             |
| III. | 88.3   | 58.1   | 36.4   | 30.7   |             |
| IV.  | 161.3  | 45.0   | 20.4   | 11.9   |             |

Detection was conventional, i.e., the HPLC mobile phase was 58% acetonitrile and 42% (0.1M acetic acid (v/v)), the column was ASI C$_{18}$ (300×3.9 mm) and the flow rate was 2 ml/min by UV at 278 nm.

EXAMPLE 44

The physiologically active agent was Ibuprofen, commercially available from, e.g., Upjohn, which is p-isobutylhydratropic acid <2'4'-isobutylphenyl propionic acid>.

In the Table below, the following combinations were used:

I. 25 mg Ibuprofen+25% isopropyl myristate in N-methyl pyrrolidone
II. 25 mg Ibuprofen+25% isopropyl myristate in N-methyl piperidone
III. 25 mg Ibuprofen+25% isopropyl myristate in N-methyl caprolactam
IV. 25 mg Ibuprofen+25% ethyl laurate in N-methyl pyrrolidone.

The results were:

|      | 2 hrs. | 4 hrs. | 6 hrs. | 8 hrs. | (μg/cm²/hr) |
|------|--------|--------|--------|--------|-------------|
| I.   | 154.0  | 95.6   | 53.9   | 49.6   |             |
| II.  | 142.0  | 79.2   | 46.1   | 40.4   |             |
| III. | 33.3   | 90.7   | 76.4   | 63.2   |             |
| IV.  | 192.8  | 93.0   | 47.5   | 40.0   |             |

Analysis was per Ali et al, *Journal of Pharmaceutical Sciences*, 70, 944 (1981), modified for a column size per Example 40.

EXAMPLE 45

The physiologically active agent was Verapamil which has the formula:

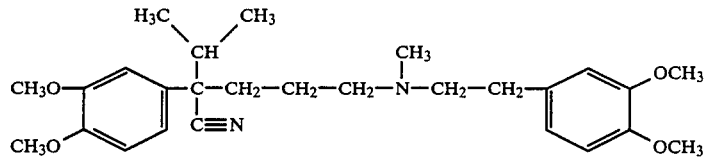

In the Table below, the following combinations were used:

I. 25 mg Verapamil+25% isopropyl myristate in N-methyl pyrrolidone
II. 25 mg Verapamil+25% isopropyl myristate in N-methyl piperidone
III. 25 mg Verapamil+25% isopropyl myristate in N-methyl caprolactam
IV. 25 mg Verapamil+25% ethyl laurate in N-methyl pyrrolidone.

The results were:

|      | 2 hrs. | 4 hrs. | 6 hrs. | 8 hrs. | (μg/cm²/hr) |
|------|--------|--------|--------|--------|-------------|
| I.   | 129.2  | 193.6  | 208.7  | 201.7  |             |
| II.  | 124.5  | 205.0  | 242.0  | 230.6  |             |
| III. | 12.1   | 55.4   | 109.5  | 132.7  |             |
| IV.  | 178.4  | 270.2  | 284.6  | 261.5  |             |

Analysis was per Watson et al, *Journal of Pharmaceutical Sciences*, 70, 800 (1981), adjusted for a different brand of column.

EXAMPLE 46

This is a "control" example.
The physiologically active agent was Nifedipine. The in vitro results are set forth below.

|   | 2 hrs. | 4 hrs. | 6 hrs. | 8 hrs. | (μg/cm²/hr) |
|---|---|---|---|---|---|
| V. | <2 | 2.7 | 8.1 | 3.9 | |

V: 25 mg Nifedipine in 1 ml of N—methyl pyrrolidone with 1 ml of sample in the diffusion cell.

EXAMPLE 47

This is a "control" example.
The physiologically active agent was Verapamil. The in vitro results are set forth below.

|   | 2 hrs. | 4 hrs. | 6 hrs. | 8 hrs. | (μg/cm²/hr) |
|---|---|---|---|---|---|
| V. | <2 | <2 | <2 | <2 | |
| VI. | 2.7 | 5.5 | 6.3 | 4.5 | |

V (Control) - 25 mg Verapamil in N—methyl pyrrolidone (1 ml)
VI (Background) - 25 mg Verapamil in dimethyl sulfoxide (DMSO) (1 ml); 1 ml in the diffusion cell.

EXAMPLE 48

The physiologically active agent was Theophyline. The in vitro results are set forth below.

|   | 2 hrs. | 4 hrs. | 6 hrs. | 8 hrs. | (μg/cm²/hr) |
|---|---|---|---|---|---|
| I. | 617 | 694 | 515 | 468 | |
| II. | 20 | 20 | 25 | 26 | |
| III. | 125 | 156 | 183 | 158 | |
| IV. | 11 | 11 | 11 | 11 | |

I. 400 mg Theophyline in 1 ml of 25% isopropyl myristate in N—methyl pyrrolidone
II. (Control) - 400 mg Theophyline in isopropyl myristate.
III. (Background) - 400 mg Theophyline in DMSO.
IV. (Background) - 400 mg Theophyline in ethyl alcohol.

EXAMPLE 49

The following in vivo examples are presented. The physiologically active agent was Diazepam* unless otherwise indicated. Direct comparisons are made to an in vitro example in certain instances.
*7-chloro-1,3-dihydro-1-methyl-5-phenyl-2H-1,4-benzodiazepin-2-one 150 mg of Diazepam was dissolved in 6 ml of 25% IPM in N,N-dimethylacetamide. To this solution was added 120 mg of hydroxypropylcellulose (Klucel® HF).

0.5 ml of the solution was placed in a polyester cup (4 cm² in diameter; 0.5 ml in volume).

The solution in the cup was placed on the monkey's chest and in the diffusion cell.

| | Monkey Plasma Level | | | | |
|---|---|---|---|---|---|
| | 1 hr | 3 hr | 5 hr | 7 hr | (ng/ml) |
| In Vivo monkey | 35 | 36 | — | 19 | |
| | Diffusion Cell; Flux Through Rat Skin | | | | |
| | 2 hr | 4 hr | 6 hr | 8 hr | μ(g/cm²/hr) |
| In Vitro Flux | 24 | 38 | 32 | 35 | |

The above procedure was duplicated except for using 25% n-dodecylchloride in N,N-dimethylactamide.
The results are set forth below.

| | 1 hr | 3 hr | 5 hr | 7 hr | (ng/ml) |
|---|---|---|---|---|---|
| In Vivo monkey | 116 | 57 | 33 | 29 | |
| | Diffusion Cell | | | | |
| | 2 hr | 4 hr | 6 hr | 8 hr | (μg/cm²/hr) |
| | 54 | 59 | 42 | 39 | |

EXAMPLE 50

The procedure of Example 38 was duplicated except for using 25% n-dodecyl chloride in N-methyl pyrrolidone with 20% PVPK-90.
The results are set forth below.

| | Monkey Plasma Level | | | | |
|---|---|---|---|---|---|
| | 1 hr | 3 hr | 5 hr | 7 hr | (ng/ml) |
| In Vivo monkey | 34 | 42 | 37 | 30 | |
| | Diffusion Cell; Flux Through Rat Skin | | | | |
| | 2 hr | 4 hr | 6 hr | 8 hr | (μg/cm²/hr) |
| In Vitro | 27 | 33 | 37 | 38 | |

EXAMPLE 51

Illustrating the therapeutically effective blood levels obtained in vivo with the rhesus monkey, the following results were obtained using Propranolol and Indomethacin.

| | | In Vivo - Monkey Plasma | | | | |
|---|---|---|---|---|---|---|
| Drug (200 mg on 49 cm²) | Vehicle | Hours (ng/ml plasma) | | | | |
| | | 1 | 2 | 3 | 5 | 5 |
| Propranolol (200 mg) | 25% Isopropyl myristate in N—methyl piperidone | 35 | 45 | 80 | 90 | 105 |
| Indomethacin (200 mg) | 25% ethyl laurate in N—methyl pyrrolidone | 370 | 505 | 420 | 225 | 110 |

Other Beta-blockers which are expected to be useful in accordance with the present invention include, e.g., the commercially available materials set forth below:

Atenolol

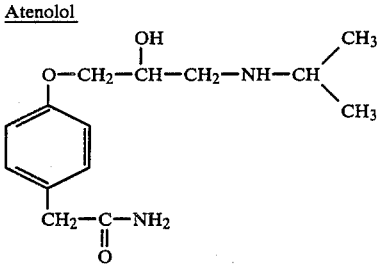

Alprenolol (HCl)

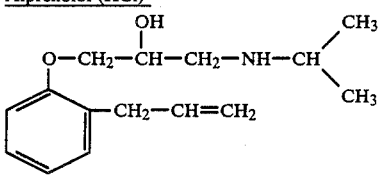

Oxyprenolol (HCl)

-continued

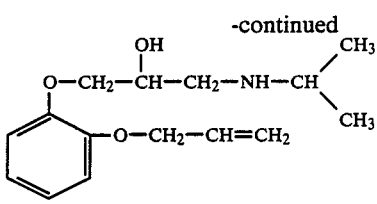

Metoprolol (tartrate)

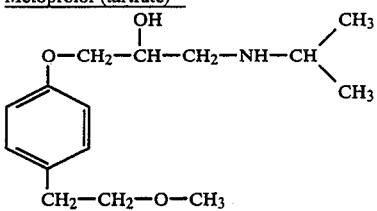

Nadolol

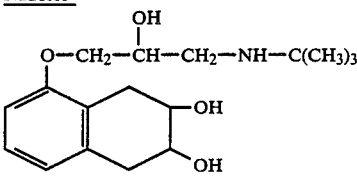

Timolol (maleate)

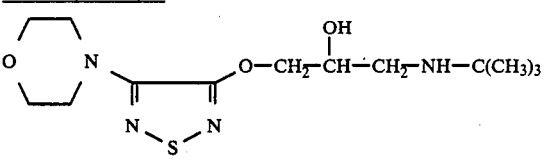

Lahetalol

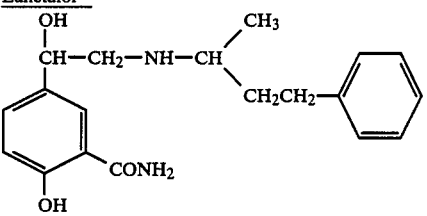

Other NSAID's which are expected to be useful in accordance with the present invention include, e.g., the materials set forth below:

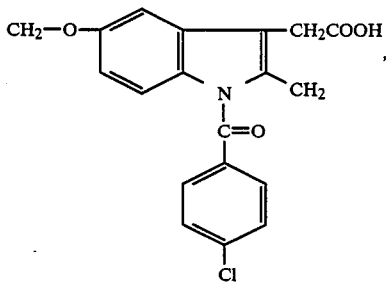

metiazinic acid, (10-Methyl-2-phenothiazinyl)acetic acid, Naproxen, (S)-6-Methoxy-2-methyl-2-naphthalen acetic acid, Ibufenac, (p-isobutyl phenyl)acetic acid, mefenamic acid, N-(2,3-xylyl)anthranilic acid (Parke-Davis), flufenamic acid, N-(3'-trifluoro-methylphenyl)-anthranilic acid (Parke-Davis), Niflumic acid, 2-(3-trifluoro methyl phenyl amino))nicotinic acid, etc.

It is to be specifically noted that Beta-blockers, benzodiazepines and NSAIDs are all recognized classes of materials which, as classes, each have a similar structure, and one skilled in the art would expect similar results from other Beta-blockers, benzodiazepines and NSAID's (nonsteroidal antiinflammatory drugs), e.g., the latter typically have carboxylic acid groups in common.

While the invention has been described in detail and with reference to specific embodiments thereof, it will be apparent to one skilled in the art that various changes and modifications can be made therein without departing from the spirit and scope thereof.

What is claimed is:

1. A method for percutaneously administering a benzodiazepine to a mammal which comprises applying the physiologically active agent to the skin of the mammal in a mixture comprising at least one of the following components A and at least one of the following components B:

Component A: an alcohol ester of an aliphatic carboxylic acid having a total number of carbon atoms of from 7 to 18 or mixtures thereof;

Component B: a compound represented by the formula:

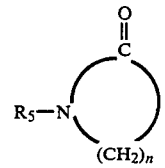

wherein $R_5$ represents a hydrogen atom or a lower alkyl group having 1 to 4 carbon atoms and n represents an integer of 3 to 5 or mixtures thereof, wherein the amount of the component A is form 0.1 to 80% by weight based on the total weight of the components A and B.

2. The method of claim 1, wherein the component A is selected from fatty acid esters represented by the formula $R_1COOR_2$ wherein the total number of carbon atoms in $R_1$ and $R_2$ is from 9 to 17 and mixtures thereof and wherein component B is a pyrrolidone-type compound represented by the formula:

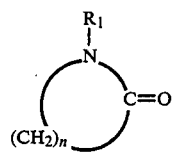

where n is an integer of 3 to 5 and $R_1$ is an alkyl group containing form 1 to 4 carbon atoms.

3. The method of claim 1 wherein the amount of component A is form 0.5 to 50% by weight based on the total weight of components A and B.

4. The method of claim 1, wherein the mixture consists essentially of the benzodiazepine, the component A and the component B.

5. The method of claim 1, wherein component A is methyl laurate, the component B is N-methyl-2-pyrrolidone and the active agent is Diazepam.

6. The method of claim 1, wherein component B is selected from the group consisting of 2-pyrrolidone, N-methyl-pyrrolidone, N-methylpiperidone, caprolactam and N-methylcaprolactam.

7. The method of claim 6, wherein the carboxylic moiety of the component A is a saturated fatty acid having 8 to 14 carbon atoms.

8. The method of claim 7, wherein the component A is selected form the group consisting of methyl laurate, ethyl laurate, butyl laurate and isopropyl myristate.

* * * * *